(12) United States Patent
Desarzens et al.

(10) Patent No.: US 7,955,320 B2
(45) Date of Patent: *Jun. 7, 2011

(54) PRECISION SPINDLE INSTRUMENT HOLDER FOR SURGICAL INSTRUMENT

(75) Inventors: Yves Desarzens, Corgémont (CH); André Lechot, Orvin (CH)

(73) Assignee: Greatbatch Medical S.A., Orvin (CH)

( * ) Notice: Subject to any disclaimer, the term of this patent is extended or adjusted under 35 U.S.C. 154(b) by 1264 days.

This patent is subject to a terminal disclaimer.

(21) Appl. No.: 10/595,442

(22) PCT Filed: Nov. 10, 2004

(86) PCT No.: PCT/IB2004/003684
§ 371 (c)(1),
(2), (4) Date: Apr. 20, 2006

(87) PCT Pub. No.: WO2005/044114
PCT Pub. Date: May 19, 2005

(65) Prior Publication Data
US 2007/0083208 A1    Apr. 12, 2007

Related U.S. Application Data

(63) Continuation-in-part of application No. 10/391,464, filed on Mar. 18, 2003, now Pat. No. 7,056,317, which is a continuation of application No. 09/902,369, filed on Jul. 9, 2001, now Pat. No. 6,540,739, which is a continuation of application No. 09/602,341, filed on Jun. 24, 2000, now Pat. No. 6,264,647.

(60) Provisional application No. 60/518,769, filed on Nov. 10, 2003.

(51) Int. Cl.
*A61B 17/00* (2006.01)
(52) U.S. Cl. .............................................. 606/1; 606/80

(58) Field of Classification Search .......... 606/1, 79–81, 606/167, 180; 279/93, 145
See application file for complete search history.

(56) References Cited

U.S. PATENT DOCUMENTS
5,236,433 A    8/1993    Salyer
(Continued)

*Primary Examiner* — Ahmed M Farah
(74) *Attorney, Agent, or Firm* — Michael F. Scalise

(57) ABSTRACT

A surgical instrument holder (10) is made up of a head assembly (68) and a drive spindle assembly (42). The head assembly (68) has a shank (12) with a first driveable end (14) and second coupling end (16). The second end has a coupling device (20) having an interface (22) for receiving a surgical instrument (24). The instrument (24) is held in functional assembly to the shank by a releasable locking mechanism (26). The releasable locking mechanism (26) is made up of a locking ring (30) slideably disposed about the shank, a spring (32) biased against the coupling device (20) by the locking ring, and a connection ring (34) retaining the locking ring in a fixed position during use. The drive spindle assembly (42) is connected to the head assembly (68) so as to transmit torque therethrough. The spindle assembly (42) has an elongated drive spindle (40), high precision bearings (44, 120, 122) and a cylindrical tube (46). The drive spindle (40) is releasably mounted to an end (36) of the spindle assembly and is supported for rotation within the cylindrical tube (46) by the high-precision bearings disposed therebetween and held in place at least in part by the shank (12). The bearings (44) precisely control the position of a surgical instrument (24) affixed thereto. The connection ring (34) provides a common quick-release connection with the head assembly (68) and the drive spindle assembly (42), such that unlocking of the connection ring (34) enables quick disassembly of the connection ring, spring (32), locking ring (30), and drive spindle assembly (42) for cleaning and component sterilization.

24 Claims, 4 Drawing Sheets

U.S. PATENT DOCUMENTS

| | | |
|---|---|---|
| 5,658,290 A | 8/1997 | Lechot |
| 5,817,096 A * | 10/1998 | Salyer .............................. 606/81 |
| 6,102,915 A * | 8/2000 | Bresler et al. .................... 606/80 |
| 6,258,107 B1 * | 7/2001 | Balazs et al. .................. 606/153 |
| 6,264,647 B1 | 7/2001 | Lechot |
| 6,854,742 B2 * | 2/2005 | Salyer et al. .................... 279/93 |
| 7,326,198 B2 * | 2/2008 | Desarzens et al. ................ 606/1 |

* cited by examiner

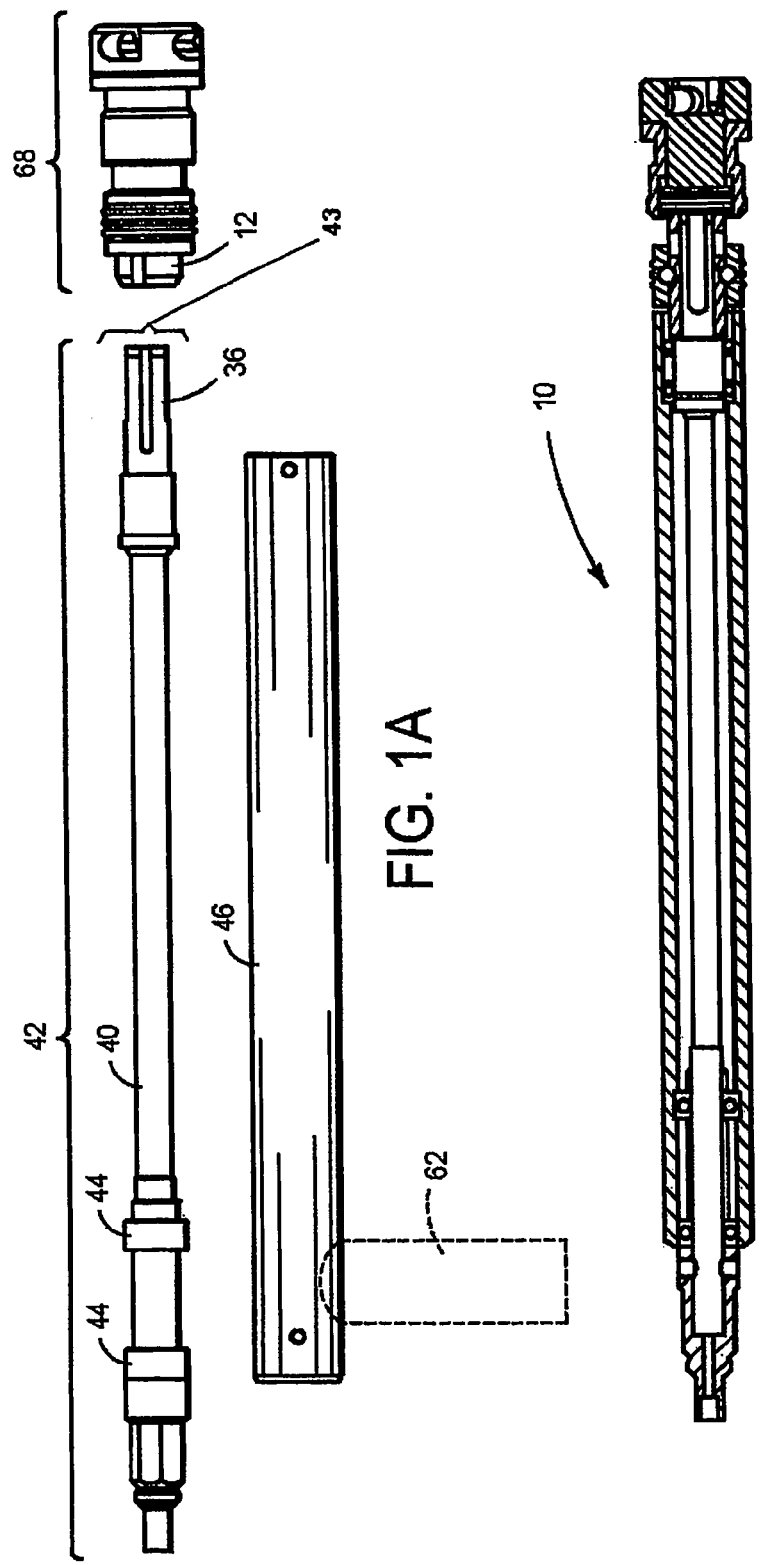
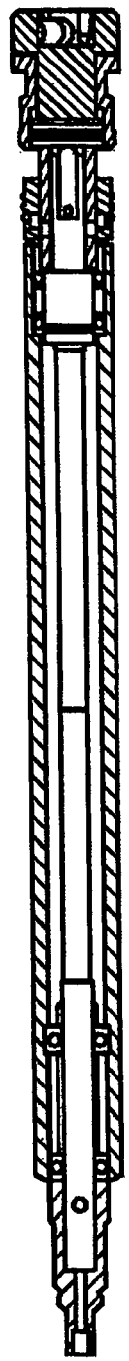
FIG. 1A
FIG. 2A
FIG. 2B

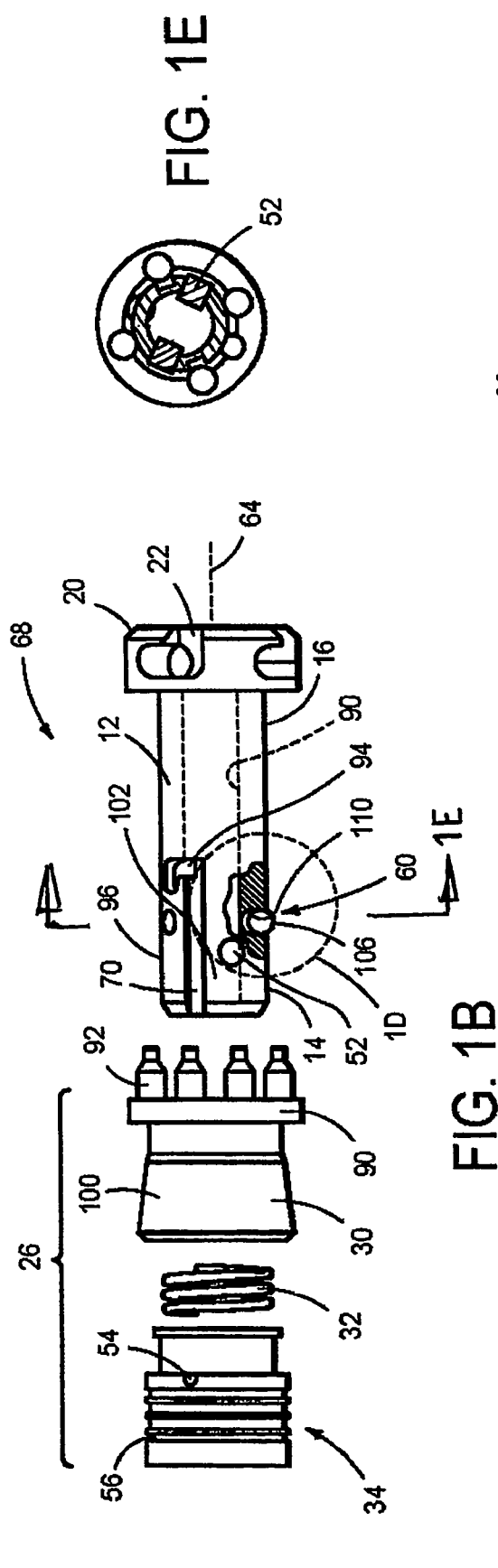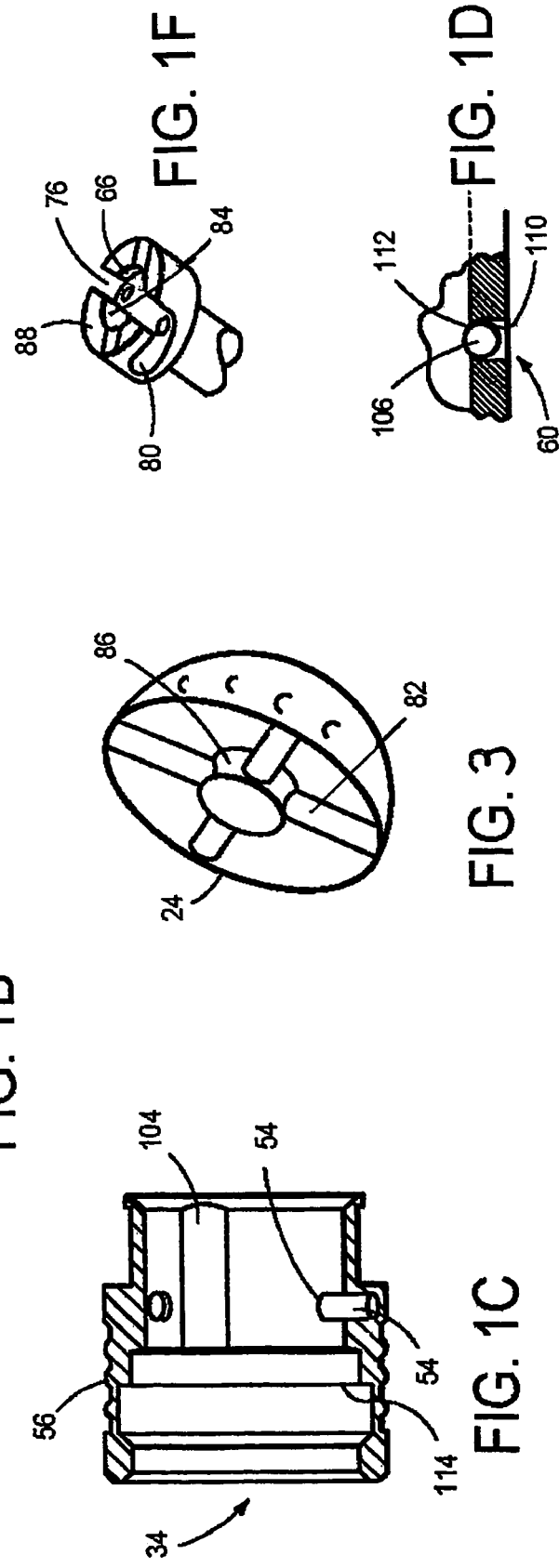

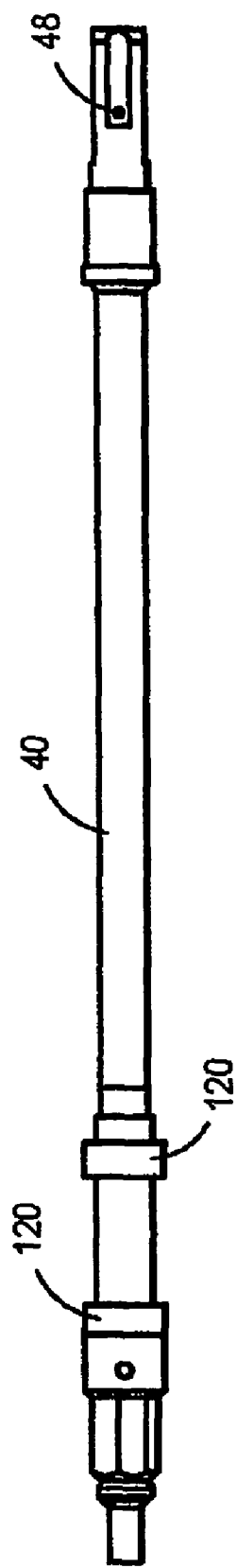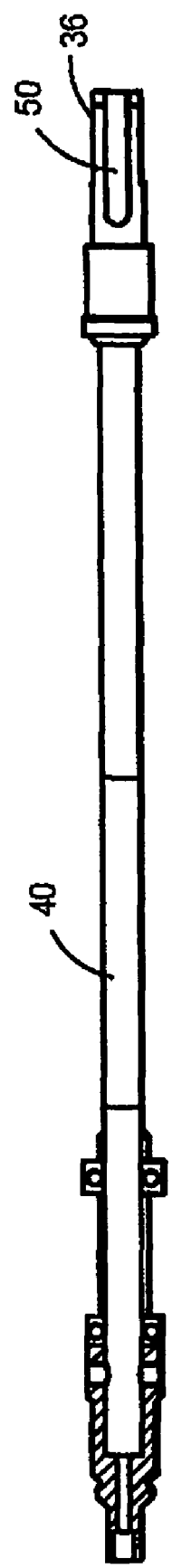
FIG. 4A
FIG. 4B

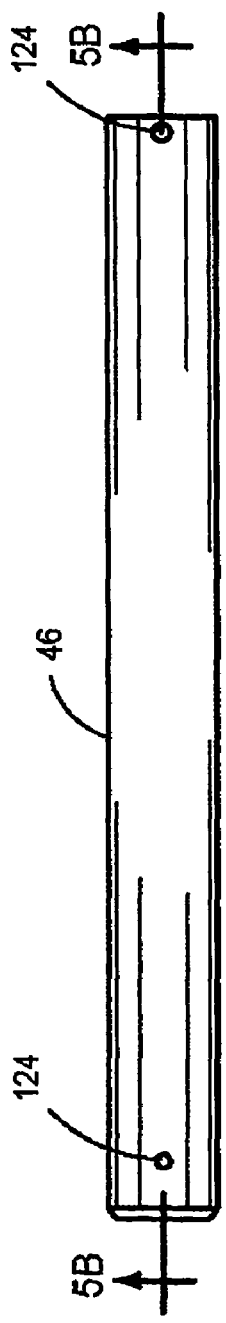
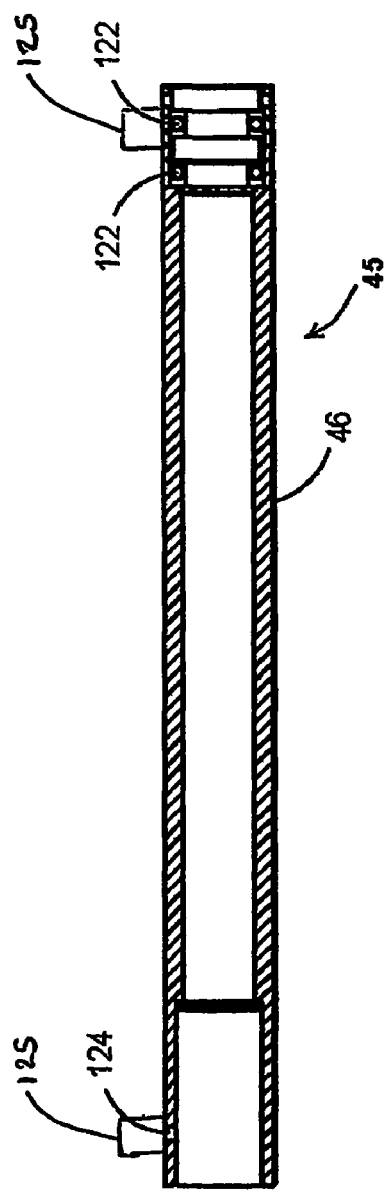
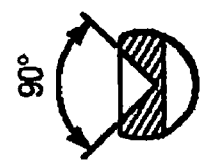

PRECISION SPINDLE INSTRUMENT HOLDER FOR SURGICAL INSTRUMENT

RELATED APPLICATIONS

For the purposes of the United States, this application is a continuation-in-part which is continuation of Ser. No. 10/391,464, filed Mar. 18, 2003 now U.S. Pat. No. 7,056,317, which is a continuation of Ser. No. 09/902,369 filed on Jul. 9, 2001 now U.S. Pat. No. 6,540,739, which in turn is a continuation of Ser. No. 09/602,341 filed Jun. 24, 2000 and now U.S. Pat. No. 6,264,647 issued Jul. 24, 2001. Priority is claimed to U.S. Ser. No. 60/518,769, filed Nov. 10, 2003 which is incorporated herein by reference thereto.

BACKGROUND OF THE INVENTION

The invention relates to an instrument holder for a surgical instrument, comprising a shank equipped with a head designed to receive an instrument, and an annular locking component mounted so as to slide about the shank, under the head, equipped with locking means which cooperate with the head so as to lock the instrument on the head, and pushed against the head by a helical spring.

An instrument holder of this type is known in particular from U.S. Pat. Nos. 5,658,290 and 5,236,433, the contents of which are incorporated herein by reference.

A surgical instrument, for example for preparing for the fitting of a hip prosthesis, works in a medium which causes considerable soiling of the instrument and the instrument holder. Moreover, a surgical instrument holder must be cleaned very frequently and very carefully in order to avoid any risk of infection. However, cleaning of surgical instruments is difficult, in particular the cleaning of the space between the shank and the locking component on account of the presence of bone debris and coagulated blood.

Still further, tools designed to meet the requirements of manual control in which sufficient tactile feedback is essentially the only instrument control design criteria are often not adequate when applied to modern surgical procedures, such as Computer Assisted Orthopedic Surgery (CAOS) that requires greater precision in order to enable fixed position sensors to transmit accurate position information. CAOS requires attachment (and detachment) of devices that hold or locate IR detectable markers.

What is needed therefore is an instrument holder that facilitates calibration of CAOS systems by the reproducible repositioning with each attachment and after cleaning. Further, what is needed is an instrument holder that is simple to disassemble for cleaning without special tools, and which precisely controls the position of the held instrument in order to enable position sensors to transmit position information accurate enough to enable remote, computer assisted orthopedic surgical procedures.

SUMMARY OF THE INVENTION

A surgical instrument holder is made up of a head assembly and a drive spindle assembly. The head assembly has a shank with a first driveable end and second coupling end. The second end has a coupling device having an interface for receiving a surgical instrument. The instrument is held in functional assembly to the shank by a releasable locking mechanism. The releasable locking mechanism is made up of a locking ring slideably disposed about the shank, a spring biased against the coupling device by the locking ring, and a connection ring retaining the locking ring in a fixed position during use. The drive spindle assembly is connected to the head assembly so as to transmit torque therethrough. The spindle assembly has an elongated drive spindle, high-precision bearings and a cylindrical tube. The drive spindle is releasably mounted to an end of the spindle assembly and is supported for rotation within the cylindrical tube by the high-precision bearings disposed therebetween and held in place at least in part by the shank. The bearings precisely control the position of a surgical instrument affixed thereto. The connection device provides a common quick-release connection with the head assembly and the drive spindle assembly, such that unlocking of the connection device enables quick disassembly of the connection ring, spring, locking ring, and drive spindle assembly for cleaning and component sterilization.

The object of the invention is to provide optimum conditions for rapid cleaning and precise control of the position of the spindle during operation, in order that position sensors mounted on the spindle can transmit accurate position information for computer assisted surgery.

To this end, the instrument holder according to the invention has a quick release head which holds the instrument, the head being releaseably connected to a precision spindle supported in rotation by bearings mounted between the shaft and an outer bearing tube. The spring bears on a locking ring sliding on the shank, and the shank and the locking ring have manually activated means of connection by rotation of the connection ring in such a way that such motion permits release of the connection ring thereby allowing the locking ring, the spring and the connection ring to slide freely on the shank. This almost instantaneous disassembly of the component parts of the instrument holder allow it to be thoroughly and quickly cleaned.

In turn, after removal of the quick release head, the precision spindle may be easily disassembled for cleaning simply by removing the subassembly comprising the spindle and attached bearing from the subassembly comprising the bearing tube and internally mounted bearing.

In an advantage of the invention, the fastening and release of the locking ring takes place instantaneously, which represents a time savings. This makes it possible to ensure that a complete kit of instruments is not rendered unusable because of a single component being inoperative.

BRIEF DESCRIPTION OF THE DRAWINGS

The attached drawing shows an embodiment of the invention by way of example.

FIG. 1A is an exploded view of the instrument holder of the invention in the disassembled position.

FIG. 1B is an exploded view of the head of the instrument holder is a disassembled position.

FIG. 1C is a cross-sectional view of the locking ring of the invention.

FIG. 1D is a detail view of the area A of FIG. 1B of the invention.

FIG. 1E is a rear, cross sectional view taken through the pins of the shank of the invention.

FIG. 1F is a perspective view of the head of the head assembly of the invention.

FIG. 2A is an assembled, cross sectional view of the instrument holder in the locked position, taken through the ball-detents.

FIG. 2B is an assembled, cross sectional view of the instrument holder taken 90 degrees from that of FIG. 2A, in the locked position.

FIG. 3 is a perspective view of a surgical instrument for use with the invention.

FIG. 4A is a side view of a central drive shaft having a bearing attached thereto.

FIG. 4B is a partial cross sectional view of the drive shaft of FIG. 4A.

FIG. 5A is a side view of the spindle cover tube of the invention.

FIG. 5B is a cross sectional side view of the spindle tube of the invention.

FIG. 5C is a front view of the spindle cover tube of the invention.

FIG. 5D is a detail view of a location divot of the invention.

DETAILED DESCRIPTION OF THE PREFERRED EMBODIMENT(s)

Referring now to FIGS. 1A-1F, and 2A-2B, a surgical instrument holder 10 has a spindle assembly 42, a cylindrical shank 12 at one end of which a head 20 is fixed which is essentially identical to the head described in U.S. Pat. No. 5,658,290, the contents of which are incorporated by reference thereto. The shank 12 has a driveable end 14 and a coupling end 16. The coupling end 16 is made up of a coupling device 20 having an interface 22 for receiving a surgical instrument 24, shown in FIG. 3. The surgical instrument 24 is held in functional assembly to the shank by a releasable locking mechanism 26. The locking mechanism 26 includes a locking ring 30 slideably disposed about the shank, a spring 32 biased against the coupling device 20 by the locking ring, and a connection ring 34 retaining the locking ring in a fixed position during use. The spring 32 is preferably a helical compression spring.

The shank 12 is releasably mounted to an end 36 of an elongated drive spindle 40 of a drive spindle assembly 42. The drive spindle assembly 42 has the drive spindle 40, high-precision bearings 44, 120, 122 and a cylindrical tube 46. The drive spindle 40 is supported for rotation within the cylindrical tube 46 by the high-precision bearings 44, 120, 122 disposed therebetween. The bearings 122 are retained by the shank 12. The bearings 44, 120, 122 precisely control the position of a surgical instrument 24 relative to position sensors 124 mounted on the tube. The end 36 of the drive spindle 40 has a keyway 50 which cooperates with a key or pin 52 on the shank 12 in order to impart a torque into the shank 12 when driving an instrument 24. The shank 12 is locked on the drive spindle 40 via the balls 106, which lock into divots 48 upon actuation by the common connection ring 34, thereby providing a common quick-release connection with the shank 12. Thus, unlocking of the connection ring 34 enables quick disassembly of the connection ring, spring 32, locking ring 30, and drive spindle assembly 42 for cleaning and component sterilization.

The locking ring 30 of the releasable locking mechanism 26 is moveable in a locking direction to lock the instrument 24 onto the interface 22. The locking direction is toward the coupling end 16 of the shank 12.

The connection ring 34 includes at least one pin 54 mounted in a coupling sleeve 56. The spring 32 is biased against the coupling sleeve 56 by the locking ring 30. The sleeve 56 is slideable about the shank 12 so as to operate a ball-detent 60.

The connection ring 34 locks over the shank 12. Optionally, the shank 12 may have a smaller diameter, or smaller local diameter (for example, by longitudinal flats cut onto the cylindrical surface of the shaft) than the coupling end, so that when the locking ring 30 is unlocked and slid back along the shank, cleaning access to all surfaces of the locking mechanism is facilitated.

Referring again to FIGS. 1B and 1F, the interface is a recess 22 in the head 20 of the coupling end 16 of the shank 12. The recess 22 is cylindrical and coaxial with a central axis 64 of the shank 12. A chamfered surface 66 is disposed within the recess to align the instrument 24 axially. The interface 22 is a recess intersected by a transverse slot 76 in which a wall 80 of the slot engages a corresponding surface 82 of the instrument 24. The recess 22 includes a seat 84 shaped to receive the end of the instrument 24 about its circumference 86.

This head 20 has a central recess 84. The head forms a crown 88 around this recess. This crown 88 has four bayonet catches 22 diametrically opposite in pairs. A reamer 24 analogous to the reamer shown and described in U.S. Pat. No. 5,658,290 is fixed in these catches 22. The reamer 24 is locked in the catches 22 by the annular locking ring 30 equipped with a plate 90 having four parallel fingers 92 which pass through the head 20 in order to close the bayonet catches 22, in a manner as is described in U.S. Pat. No. 5,658,290.

The locking ring 30 slides on the shank 12. At least one bayonet catch 94 is formed at the end 96 of the shank 12 remote from the head 20. These catches 22 are preferably at least two in number and diametrically opposed to facilitate assembly, as is explained below. Also arranged around this shank 12 is a helical spring 32 which engages in a frustoconical widened part 100 of the locking ring 30 and bears against this locking ring, and which slides freely on the shank 12. The assembly of the instrument holder head 20 is completed by a connection ring 34 which also slides on the shank 12 and is equipped internally with a radial stud 54 that is captured in a keyway 102, thus permitting the connection ring to move axially along the shank 12, and eventually into the bayonet recess 94.

The locking ring 30 is disposed in the coupling end 16 of the shank 12. The locking ring 30 activates at least one ball-detent 60. Preferably, the locking ring 30 activates one or more circumferentially spaced apart ball-detents 60.

The pin 54 of the connection ring 34 cooperates with a guide slot 70 and bayonet landing 94 to lock the connection ring 34 on the shaft 12.

The ball-detent 60 is received into a recess 110 in the instrument bolder, the connection ring 34 sliding over the ball detent 60 to bias a ball 106 into a recess 48 in the drive spindle 46 to lock the shank 12 onto the drive spindle in a manner to lock the assembly 42 including the bearings 44 in place.

Starting from the disassembled position shown in FIGS. 1A-1B, and in order to assemble the instrument holder 10, the locking ring 30 is brought under the head 20, engaging its locking fingers 92 through the head. Then, with the connection ring 34, the spring 32 is pushed against the locking ring 30 and this spring is compressed, at the same time turning the connection ring 34 axially counterclockwise until its stud 54 engages in the bayonet catch 94 in which the connection ring 34 locks by holding the connection ring 34 which is pushed rearward by the spring 32. The instrument holder 10 can then be used as is described in U.S. Pat. No. 5,658,290. The frustoconical widened part 100 provides a grip for the thumb and index finger for pulling the locking ring 30 back counter to the action of the spring 32 in order to release the instrument 24 fixed on the instrument holder 10.

Note that the connection ring 34 has two opposing channels or recesses 104 which provide clearance for ball-detents 60 during assembly and disassembly of the head assembly 68. This is because the balls 106 do not retract all the way into corresponding ball recesses 110 in the shank 12 as they are blocked by a spherical end portion 112 at the bottom of the recess 110. They may also be retained against disassembly by staking the edge of the recess 110 after the ball 106 is placed therein. When the connection ring 34 is turned, however, the opposing recesses 104 are no longer aligned with the balls 106, thereby enabling the shoulder 114 to be biased against the balls 106 by the force of the spring 32, thus pressing the balls further into their recesses 110 such that the ends of the balls protrude into divots or seats 48 (shown in FIG. 4A) in the end of the spindle 40 which is aligned under the balls by a positioning shoulder and the opposing longitudinally oriented keyways 50 into which pins 52 engage on assembly.

Conversely, in order to disassemble the instrument holder 10, it suffices to first push the connection ring 34 forward counter to the action of the spring 32. This removes the wedging bias on the balls 106 into seats 48 in the end of the spindle 40, the bias otherwise removing play in the assembly. The surgeon then turns the connection ring axially clockwise to align the balls 106 with the opposed clearance recesses 104, to enable the balls 106 to further retreat from the recess 110, so as to enable the user to disconnect the spindle assembly 42 from the head assembly 68 by drawing it out as the connection ring 34 is held against the bias of the spring 32. Concurrently, the turning of the connection ring 34 in the clockwise direction removes the stud 54 from the bayonet catch 94, thus enabling the surgeon to remove the connection ring 34 from the shank 12, and then the spring 32, followed by the locking ring 30 as well.

As is shown in FIG. 1B, the connection ring, spring and locking ring 34, 32 and 30, respectively, can be completely removed from the shank 12. Note that the connection ring 34 could also be removably fastened to the shank 12 by screwing, that is to say having a screw thread (not shown) in the connection ring 34 which threads onto corresponding threads (not shown) on the shank 12. Note as well that the head 20 and the fingers 92 are only one example of many alternative means of connecting to an instrument 24.

The spindle assembly 42 is also easy to disassemble in that, as shown in FIGS. 4A and 4B, bearings 120 are affixed to the outside surface of the spindle 40 and bearings 122 (shown in FIG. 5B) are affixed to the inside surface of the cover tube 46, thus permitting the tube to be slid off the spindle assembly 42 after removal of the head assembly 68. The spindle tube 46 has position sensor locator divots 124 to enable accurate and repeatable positioning of the position sensors on the tube.

In an alternate embodiment, a handle 62 is attached to the elongated spindle assembly 42.

The object of the invention is to provide optimum conditions for rapid cleaning and precise control of the position of the spindle during operation, in order that position sensors 125 mounted on the spindle cover 46 can transmit accurate position information for computer assisted surgery.

To this end, the instrument holder 10 according to the invention has a quick release head 68 which holds the instrument 24, the head 68 being releaseably connected to the precision spindle assembly 42 supported in rotation by bearings 44, 120, 122 mounted between the shaft 12 and an outer bearing tube 46. This almost instantaneous disassembly of the component parts of the instrument holder 10 allow it to be thoroughly and quickly cleaned.

In turn, the precision spindle 42 may be easily disassembled for cleaning simply by removing the subassembly 43 comprising the spindle 40 and attached bearings 44 from the subassembly 45 comprising the bearing tube 46 and internally mounted bearings 122.

The fastening and release of the connection ring 34 and thus the assembly/disassembly of the coupling head 68 and spindle assembly 42 takes place instantaneously, which represents a time savings. This helps ensure that a complete kit of instruments 24 is not rendered unusable because of a single component is blocked or inoperative.

In an advantage of the invention, the fastening and release of the connection ring takes place instantaneously, which represents a time savings. This makes it possible to ensure that a complete kit of instruments is not rendered unusable because of a single component being inoperative.

In an object of the invention, an instrument holder 10 is provided which facilitates calibration of CAOS systems by the reproducible repositioning with each attachment and after cleaning.

In a further object of the invention, an instrument holder 10 is provided that is simple to disassemble for cleaning without special tools, and which precisely controls the position of the held instrument in order to enable position sensors to transmit position information accurate enough to enable remote, computer assisted orthopedic surgical procedures.

Although illustrative embodiments of the invention have been shown and described a wide range of modification, change and substitution is contemplated in the foregoing disclosure and in some instances, some features of the present invention may be employed without a corresponding use of the other features. Accordingly it is appropriate that the appended claims be construed broadly and in a manner consistent with the scope of the invention.

What is claimed is:

1. A surgical instrument holder comprising:
 a) a head assembly having a shank with a first driveable end and second coupling end, the second end comprising a coupling device having an interface for receiving a surgical instrument and held in functional assembly to the shank by a releasable locking mechanism comprised of a locking ring slideably disposed about the shank, a spring biased against the coupling device by the locking ring, and a connection ring retaining the locking ring in a fixed position during use; and
 b) a drive spindle assembly connected to the head assembly so as to transmit torque therethrough, the spindle assembly comprising an elongated drive spindle, bearings and a cylindrical tube, wherein the drive spindle is releasably mounted to an end of the spindle assembly and is supported for rotation within the cylindrical tube by the bearings disposed therebetween and held in place at least in part by the shank, the bearings precisely controlling the position of a surgical instrument affixed thereto; and
 c) wherein further, the connection ring provides a common quick-release connection with the head assembly and the drive spindle assembly, whereupon unlocking of the connection ring enables quick disassembly of the connection ring, spring, locking ring, and drive spindle assembly for cleaning and component sterilization.

2. The surgical instrument holder of claim 1 wherein the locking ring of the releasable locking mechanism is moveable in a locking direction to lock an instrument onto the interface.

3. The surgical instrument holder of claim 2 wherein the locking ring is disposed in the coupling end of the shank.

4. The surgical instrument holder of claim 2 wherein the connection ring activates at least one ball-detent.

5. The surgical instrument holder of claim 4 wherein the connection ring activates at least two circumferentially spaced apart ball-detents.

6. The surgical instrument holder of claim 4 wherein the ball-detent comprises a ball received into an annular recess in the instrument holder, the locking component sliding over the ball detent to bias a ball into the recess to lock the shank onto the drive spindle in a manner to lock the cover assembly including the bearings in place.

7. The surgical instrument holder of claim 2 wherein the locking direction is toward the coupling end of the shank.

8. The surgical instrument holder of claim 1 wherein the connection ring comprises at least one pin mounted in a coupling sleeve against which the spring is biased by the locking ring, the sleeve being slideable about the shank so as to operate a ball-detent.

9. The surgical instrument holder of claim 1 wherein a handle is attached to the first end of the elongated spindle assembly.

10. The surgical instrument holder of claim 1 wherein the spindle is held within a spindle tube by the bearings providing precision rotation of the spindle with the tube, and wherein the tube is provided with position sensors, placed at predetermined locations on the tube, thereby enabling the instrument holder to participate in the communication of position information.

11. The surgical instrument holder of claim 1 wherein the interface is a recess in the coupling end of the shank.

12. The surgical instrument holder of claim 11 wherein the recess is cylindrical and coaxial with a central axis of the shank.

13. The surgical instrument holder of claim 12 wherein a chamfered surface is disposed within the recess to align an instrument axially.

14. The surgical instrument holder of claim 1 wherein the spring is a helical compression spring.

15. The surgical instrument holder of claim 1 wherein the connection ring cooperates with a bayonet slot to lock the connection ring on the shaft.

16. The surgical instrument holder of claim 15 wherein the pin of the connection ring locks in the bayonet slot.

17. The surgical instrument holder of the claim 16 wherein the bayonet slot is disposed on the shank.

18. The surgical instrument holder of claim 1 wherein the interface is a recess intersected by a transverse slot in which a wall of the slot engages a corresponding surface of the instrument.

19. The surgical instrument holder of claim 18 wherein the recess includes a seat shaped to receive the end of an instrument about its circumference.

20. The surgical instrument holder of claim 1 wherein the shank is hollow along its length so as to provide a channel facilitating chip removal.

21. The surgical instrument holder of claim 1 wherein the tube includes position sensors mounted on the spindle which participate in the communication of position information to a computer to aid in computer assisted surgery.

22. The surgical instrument holder of claim 1 wherein a frustoconical widened part provides a grip for the thumb and index finger for pulling the locking ring back counter to the action of the spring in order to release an instrument fixed on the instrument holder.

23. The surgical instrument holder of claim 1 wherein the connection ring permits disconnection of the spindle assembly from the head assembly when a user holds the connection ring having an internal stud against a bias of the spring, then turns the connection ring in such a way that its stud leaves a bayonet catch so as to unlock the connection ring from the catch, the user being able to remove the connection ring from the shank, and then the spring, followed by the locking ring as well.

24. A surgical instrument holder comprising:
   a) a head assembly having a shank with a first driveable end and second coupling end, the second end comprising a coupling device having an interface for receiving a surgical instrument and held in functional assembly to the shank by a releasable locking mechanism comprised of a locking ring slideably disposed about the shank, a spring biased against the coupling device by the locking ring, and a connection ring retaining the locking ring in a fixed position during use, wherein the connection ring comprises at least one pin mounted in a coupling sleeve against which the spring is biased by the locking ring, the sleeve being slideable about the shank so as to operate a ball-detent; and
   b) a drive spindle assembly connected to the head assembly so as to transmit torque there through, the spindle assembly comprising an elongated drive spindle, bearings and a cylindrical tube, wherein the drive spindle is releasably mounted to an end of the spindle assembly and is supported for rotation within the cylindrical tube by the bearings disposed there between and held in place at least in part by the shank, the bearings precisely controlling the position of a surgical instrument affixed thereto; and
   c) wherein further, the connection ring provides a common quick-release connection with the head assembly and the drive spindle assembly, whereupon unlocking of the connection ring enables quick disassembly of the connection ring, spring, locking ring, and drive spindle assembly for cleaning and component sterilization.

\* \* \* \* \*